United States Patent [19]

Sidorenko et al.

[11] 4,224,952
[45] Sep. 30, 1980

[54] ELECTRONIC ERGOMETER

[76] Inventors: Georgy I. Sidorenko, ulitsa Pulekhova, 7, kv. 37; Vladimir I. Stankevich, ulitsa Krasnoarmeiskaya, 32, kv. 15, both of Minsk, U.S.S.R.

[21] Appl. No.: 931,525

[22] Filed: Aug. 7, 1978

[51] Int. Cl.³ ............................................. A61B 5/10
[52] U.S. Cl. ...................................... 128/782; 272/70
[58] Field of Search .............................. 128/782, 774; 272/DIG. 5, DIG. 6, 70

[56] References Cited

U.S. PATENT DOCUMENTS

| | | | |
|---|---|---|---|
| 3,505,992 | 4/1970 | Jaeger | 128/774 |
| 3,602,502 | 8/1971 | Hampl | 272/DIG. 6 |
| 3,627,313 | 12/1971 | Schonfeld | 272/DIG. 5 |
| 3,797,010 | 3/1974 | Adler et al. | 340/323 |
| 4,112,926 | 9/1978 | Schulman et al. | 128/782 |
| 4,117,834 | 10/1978 | McPartland et al. | 128/782 |

Primary Examiner—Kyle L. Howell
Attorney, Agent, or Firm—Fleit & Jacobson

[57] ABSTRACT

An electronic ergometer is placed in a housing and comprises a serial arrangement of a transducer to convert the oscillations of the body center of gravity of an individual, implemented as a seismic pickup, and a pulse shaper. Coupled to the pulse shaper is an adjustable high frequency multivibrator with a frequency generating circuit having an element coupled to a unit to select the frequency of the adjustable high frequency multivibrator. Coupled to the output of the adjustable high frequency multivibrator is a frequency divider which, in turn, is coupled to a multi-digit counter connecting an indicator. A zero setting unit is coupled to the reset inputs of the frequency divider and the multi-digit counter.

4 Claims, 13 Drawing Figures

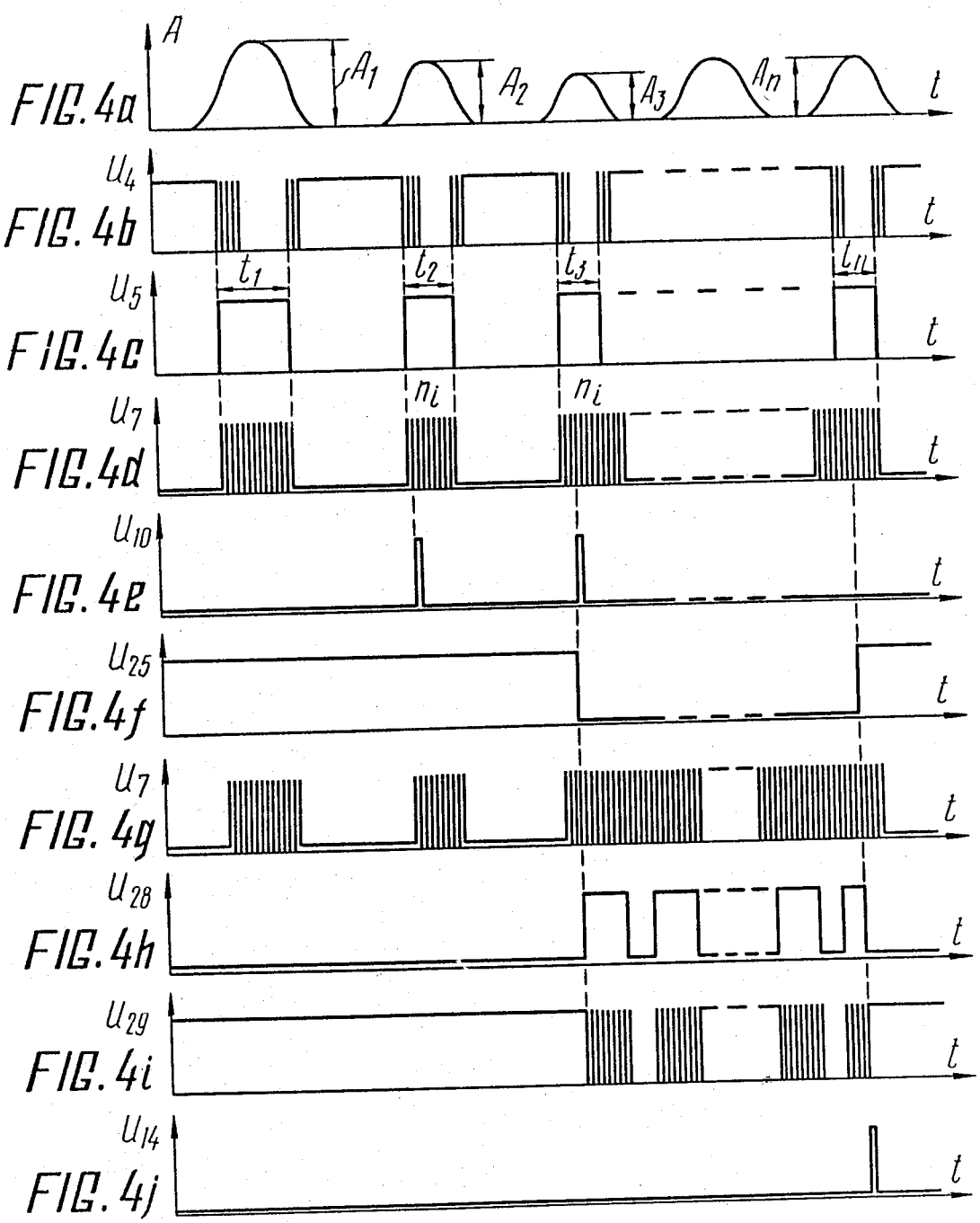

ELECTRONIC ERGOMETER

BACKGROUND OF INVENTION

1. Field of Invention

This invention relates to an apparatus for recording the loads exerted on an individual performing a movement, and more particularly to electronic ergometers.

The invention is applicable for use in medical scientific research establishments, in medical practice, in sports, in curative physical-culture exercises, and in health resort service.

2. Description of Prior Art

Known in the art is a device for estimating the work performed by an individual during walking or running (cf. the USSR Inventor's Certificate No. 469,053, Int.C. GO1C, 22/00), said device being provided with a casing which houses a transducer to convert the oscillations of the body center of gravity of an individual to electrical signals, a pulse shaper, and an electrical signal counter-/indicator, all interconnected to form a serial arrangement. A power supply unit is coupled to the pulse shaper and to the electrical signal counter/indicator. The transducer is made in the form of two pairs of contacts disposed respectively in the toe tip portion and the heel portion of an insole of a shoe. These two pairs of contacts are connected in parallel to each other, and are closed at the moment the foot touches the ground (or a support) during walking or running. The electrical signal counter/indicator is an electromechanical counter which is activated at the moment the pulse shaper produces a pulse. When at least one of the two pairs of contacts is closed, an accumulating element at the input of the pulse shaper is closed too, with the result that charge redistribution takes place and a current pulse is thus produced to activate the pulse shaper which, in turn, generates a respective pulse. The latter causes the electrical signal counter/indicator to operate and to change its reading. With the number of steps known (available from the counter/indicator), one can estimate the length of the path covered, which can be used as an indirect measure of the work performed during the movement. To this end, the number of steps is multiplied by the value of the work per step. The latter value is given by a formula in which the following parameters are interrelated: the person's own weight and height; the average rate of movement; and the average length of step.

The described device can estimate the work performed with poor accuracy since some parameters are not taken into consideration. This applies to the velocity variation during the movement and to the variation of the angle of movement relative to horizon (going upstairs or downstairs, ascending or descending movement relative to a slope plane). In addition, an individual must calculate the value of the performed work so that real-time data processing cannot be achieved in this case.

The device offers low operational convenience since it requires special-purpose shoes and leads to connect the transducer to the pulse shaper.

SUMMARY OF INVENTION

An object of the invention is to provide an electronic ergometer which can measure the work performed by an individual during a movement to a higher degree of accuracy.

Another object of the invention is to provide an electronic ergometer offering a higher operational convenience.

There is disclosed an electronic ergometer having a housing which incorporates a serial arrangement of a transducer to convert the oscillations of the body center of gravity of an individual to electrical signals and a pulse shaper, an electrical signal counting/indicating unit being coupled to the pulse shaper, the transducer being implemented, according to the invention, as a seismic pickup, the electrical signal counting/indicating unit being provided with a serial arrangement of a multi-digit counter and an indicator, in which ergometer there are provided an adjustable high frequency multivibrator with a frequency generating circuit, the control input of the multivibrator being coupled to the output of the pulse shaper, a unit to select the multivibrator frequency, having its output coupled to the frequency generating circuit, a frequency divider whose counting input is coupled to the output of the adjustable high frequency multivibrator and whose output is coupled to the counting input of the multi-digit counter, and a zero setting unit whose output is coupled to the reset inputs of the frequency divider and the multi-digit counter.

Advantageously, the transducer to convert the oscillations of the body center of gravity to electrical signals further comprises, in order to provide for higher accuracy with which the work performed by an individual is measured, at least one seismic pickup, while the pulse shaper comprises a plurality of threshold elements, equal in number to the number of seismic pickups and coupled to the outputs of the main and additional seismic pickups, and an adder coupled to the outputs of the threshold elements.

Preferably, the ergometer further comprises, in order to provide for checking the permissible value of the work performed by an individual, a unit to select the permissible value of the work performed by an individual, said unit being implemented as two switches, each being coupled to a respective high-order bit position of the multi-digit counter; a comparison circuit having its inputs coupled to the switches, and having its output coupled to the enable input of the adjustable high frequency multivibrator and to the enable input of the frequency divider; a low frequency multivibrator whose input is coupled to the output of the comparison circuit; and a mixer having its inputs coupled respectively to the outputs of the high frequency multivibrator and the low frequency multivibrator, and having its output coupled to the electrical signal counting/indicating unit.

Since the transducer and other units of the circuitry are installed in a common housing, operational convenience of the ergometer is increased and neither special-purpose shoes nor connecting leads are required.

BRIEF DESCRIPTION OF DRAWINGS

The instant invention will now be described, by way of example, with reference to the accompanying drawings in which:

FIGS. 4a, b, c, d, e, f, g, h, i, j are timing diagrams to describe how the amplitudes of the signals applied to the seismic pickups and the voltages at the outputs of respective units vary with time, according to the invention.

Figure 1:
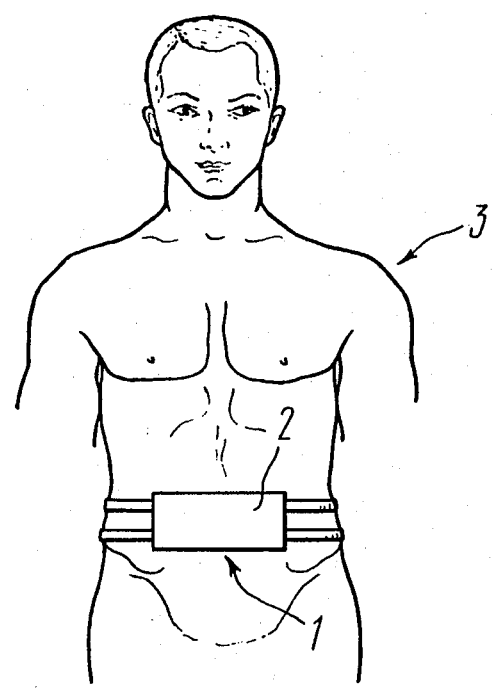
FIG. 1 shows how an electronic ergometer is arranged on an individual, according to the invention.
Figure 2:
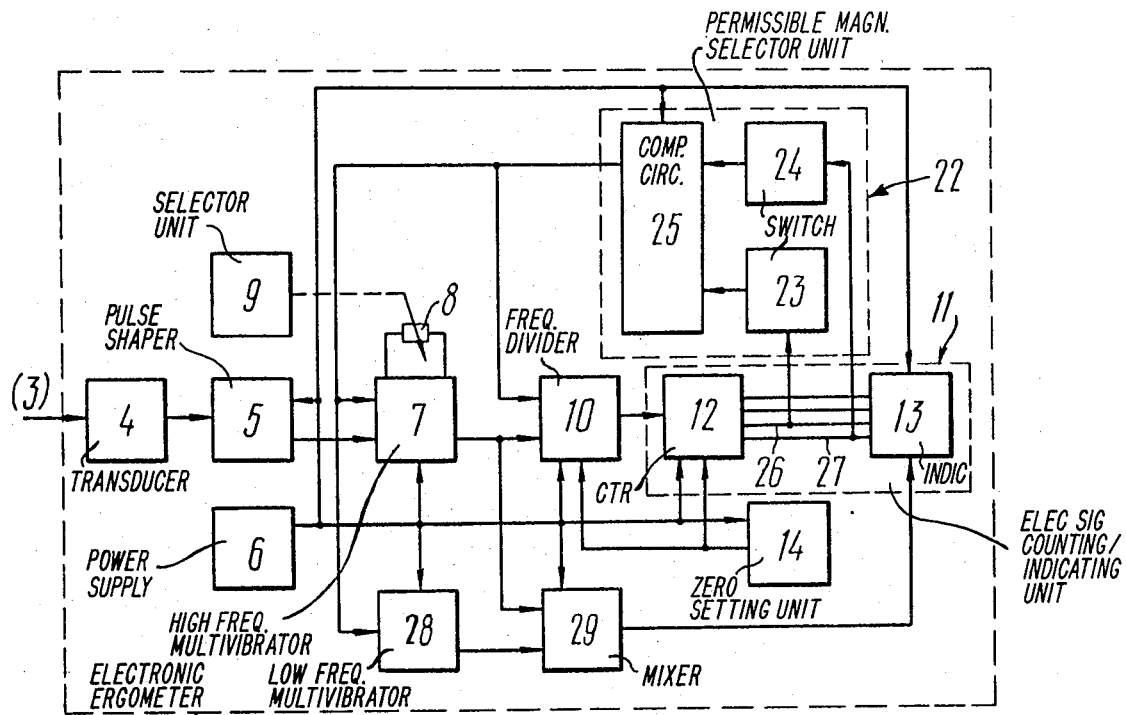
FIG. 2 is a block diagram of the electronic ergometer, according to the invention.

The electronic ergometer 1 (FIG. 1) according to the invention is installed in a housing 2 and is arranged on an individual 3. The oscillations of the body center of gravity of the individual 3 give influence on a transducer 4 (FIG. 2) designed to convert these oscillations to electrical signals. The transducer 4 is implemented as a seismic pickup whose output is coupled to a pulse shaper 5. The latter is made as a threshold element. The electronic ergometer 1 also comprises a power supply unit 6 coupled to the pulse shaper 5. Coupled to the output of the pulse shaper 5 is the control input of an adjustable high frequency multivibrator 7 with a frequency generating circuit in which a variable resistor 8 (or a variable capacitor) is connected.

The variable resistor 8 is connected mechanically with a unit 9 to select the frequency of the multivibrator 7, said unit 9 being implemented as a set of switches (not shown). The power supply unit 6 is coupled to the multivibrator 7. The output of the multivibrator 7 is coupled to the counting input of a frequency divider 10 which is coupled to the power supply unit 6. The frequency divider 10 has a reset input and an enable input. The electronic ergometer 1 is provided with an electrical signal counting/indicating unit 11 which comprises a four-digit counter 12 having a counting input, a reset input and four outputs according to the number of the bit positions in an indicator 13. The four-digit counter 12 and the indicator 13 are coupled to the power supply unit 6. The counting input of the four-digit counter 12 is coupled to the output of the frequency divider 10, whereas the four outputs of the four-digit counter 12 are coupled to the indicator 13. The latter produces a sound signal and visual digital indications to represent the magnitude of the work performed by the individual 3.

There is also provided a zero setting unit 14 having its output coupled to the reset inputs of the frequency divider 10 and the four-digit counter 12.

Figure 3:
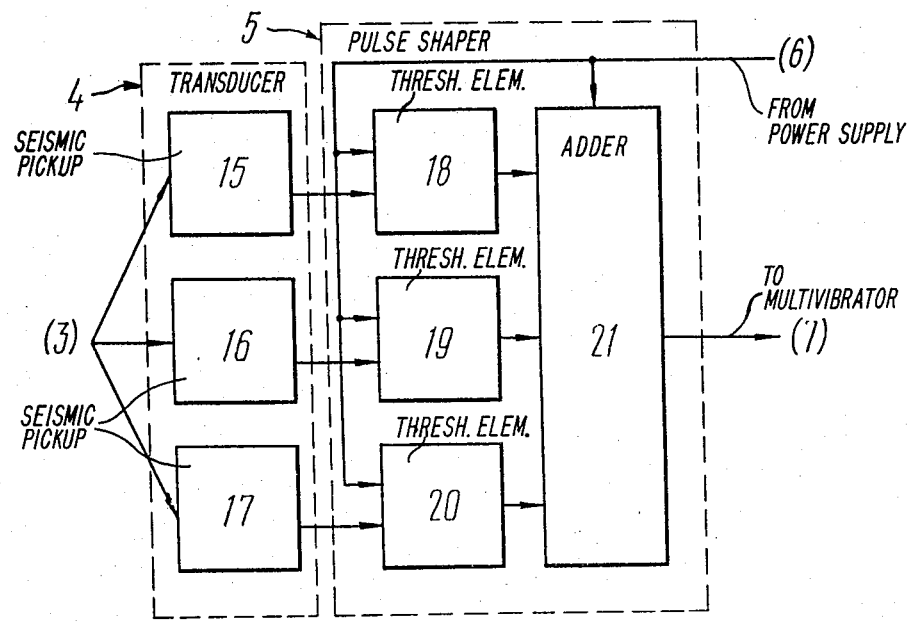
FIG. 3 is a block diagram of the pulse former and the transducer of another embodiment of the electronic ergometer, according to the invention.

To obtain data about the work performed by the individual 3, with the body center of gravity oscillating relative to three planes, the transducer 4 (FIG. 3) is used, which transducer 4 incorporates three seismic pickups 15, 16, 17. In this embodiment, the pulse shaper 5 comprises three threshold elements 18, 19, 20 coupled respectively to seismic pickups 15, 16, 17. The outputs of the threshold elements 18, 19, 20 are coupled to the inputs of an adder 21 which is an OR gate. The number of the inputs of the adder 21 is equal to the number of the threshold elements 18, 19, 20. The output of the adder 21 serves as the output of the pulse shaper 5 and is coupled to the control input of the multivibrator 7. The threshold elements 18, 19, 20 and the adder 21 are coupled to the power supply unit 6.

In order to monitor and indicate the permissible magnitude of the work performed by the individual 3, the electronic ergometer 1 (FIG. 1) further comprises a unit 22 (FIG. 2) to select that permissible magnitude. The unit 22 is implemented as two switches 23, 24 and a comparison circuit 25. The latter is a multi-input AND gate. The number of the inputs of the comparison circuit 25 corresponds to the number of the outputs of the third and fourth bit positions of the four-digit counter 12. The switch 23 has its input coupled to an output 26 belonging to the output of the third bit position of the four-digit counter 12, while the switch 24 is coupled to an output 27 belonging to the output of the fourth bit position of the four-digit counter 12. The comparison circuit 25 is coupled to the power supply unit 6. The output of the comparison circuit 25 is coupled to the enable input of the frequency divider 10 and to the enable input of the adjustable high frequency multivibrator 7. To detect and indicate the moment when the permissible magnitude of the work performed by the individual 3 is reached, a low frequency multivibrator 28 and a mixer 29 are provided. The mixer 29 is a two-input AND gate. The output of the comparison circuit 25 is coupled to the input of the low frequency multivibrator 28. The inputs of the mixer 29 are coupled respectively to the outputs of the adjustable high frequency multivibrator 7 and the low frequency multivibrator 28. The output of the mixer 29 is coupled to the indicator 13. The low frequency multivibrator 28 and the mixer 29 are coupled to the power supply unit 6. The housing 2 (FIG. 1) of the electronic ergometer 1 is fixed to the waist-band of the individual 3.

The electronic ergometer 1 operates in the following manner. The oscillations of the body center of gravity of the individual 3 are converted in the ergometer 1 to electrical signals whose widths are proportional to the oscillations amplitudes. An electrical signal from the seismic pickup of the transducer 4 (FIG. 2) is given high frequency pulses produced by the adjustable high frequency multivibrator 7. The repetition rate of the pulses generated in the multivibrator 7 is determined with the help of the frequency selector unit 9 depending on the specific data pertaining to the individual 3, such as the weight, height, average length of step and average rate of movement. The frequency divider 10 provides a pulse equivalent of 100 kg-m. The performed work amounts to 100 kg-m with a minimum error of measurement and with a given capacity of the four-digit counter 12.

The calculation of the work performed by individuals having different weight, height and other different characteristics gives the magnitude of the work per step ranging from 8 to 30 kg-m. If a 10 kg-m unit is chosen for the calculation, the magnitudes of the performed work per step represented by whole numbers, for example, 16 and 23 kg-m, cannot be obtained in each case. On the other hand, a 100 kg-m unit causes in increased discreteness and, therefore, greater measurement errors. The decimal number system, which is a most habitual for men, was selected to represent the measurement results.

The pulses produced by the frequency divider 10 are counted by the four-digit counter 12 and are displayed by the indicator 13.

After the power supply unit 6 is turned on, the four-digit counter 12 and the frequency divider 10 assume the zero state under the action of a signal delivered from the output of the zero setting unit 14. During walking or running, an individual performs oscillatory moments. The amplitude of oscillations of the body center of gravity of the individual 3 depends on his pecularities, including the walk, and amounts, on the average, to 3–4 cm. These oscillations are transferred, via the housing 2, to the electronic ergometer 1, and the transducer 4 converts the amplitude A of the body center of gravity of the individual 3 to an electrical signal (FIGS. 4a, b). This signal is applied to the input of the pulse shaper 5 whose output produces pulses $U_5$ (FIG. 4c) delivered to the control input of the adjustable high frequency multivibrator 7. The width of the pulses $U_5$ is proportional to the amplitude A of the body center of gravity of the individual 3($t_1 \sim A_1$; $t_2 \sim A_2$; $t_3 \sim A_3$; $t_n \sim A_n$). At the moment when a pulse is applied to the control input of the multivibrator 7, the latter produces a high frequency signal. As a result, the output of the multivibrator 7 provides trains of pulses $U_7$ (FIG. 4d). The number of the pulses $U_7$ in a train depends on the width of the control pulse and on the frequency to which the multivibrator 7 is adjusted.

The frequency of the pulses $U_7$ depends on the resistance value of the frequency generating circuit 8 and is selected with the help of the frequency selector unit 9. The switch (not shown) of the frequency selector unit 9 is moved to a position corresponding to the magnitude of the work performed by the individual 3 per step. This magnitude depends on the person's own weight, height, average rate of movement and average length of step and amounts, on the average, to 8–30 kg-m.

For each individual, the work performed per step is calculated using appropriate tables, monograms or a formula. Tha latter is derived on the basis of a known method dealing with the determination of the work performed by the kinematic links (hands and legs) of an individual, which method provides for the summation of the magnitudes of work performed by each link. The above tables or monograms contain the values of the abovedescribed characteristics of different individuals. With these values selected for an individual, it is possible to determine the magnitude of the work he performs per step and to introduce that magnitude into the electronic ergometer 1 by operating the switch of the frequency selector unit 9. With the latter, the frequency of the multivibrator 7 is adjusted in a range between 3.36 and 12.6 kHz.

The frequency of the multivibrator 4 is selected depending on the magnitude of the work performed by the individual 3 in a range between 8 and 30 kg-m. The train of pulses from the output of the multivibrator 7 are applied to the counting input of the frequency divider 10. The division factor of the frequency divider 10, equal to 4096, and the adjustment range of the frequency of the multivibrator 7 are selected so that a higher accuracy is attained in calculating the work performed by the individual 3. With the 4096th ($n_i$th) pulse applied to the input of the frequency divider 10, the output of the latter provides a pulse $U_{10}$ (FIG. 4l) which is equivalent of 100 kg-m. The pulses are counted by the four-digit counter 12 and are displayed by the indicator 13. At the end of operation, the electronic ergometer 1 assumes the 0 state with the help of the zero setting unit 14.

The work performed by the individual 3 can be recorded using the transducer 4 (FIG. 3) comprising three seismic pickups 15,16,17 designed to sense the oscillations of the body center of gravity of the individual 3 as occurring in three respective planes during his movement as follows: upward and downward; to and fro; to the left and to the right. If necessary, any desirable number of seismic pickups can be used. The width of the signal $U_4$ from the output of any one of the seismic pickups 15,16,17 is proportional to the amplitude A of the oscillations of the body center of gravity of the individual 3 occurred in a respective plane (FIGS. 4a, b). The signals $U_4$ from the outputs of the seismic pickups 15,16,17 are applied to the inputs of respective threshold elements 18,19,20 of the pulse shaper 5, whose outputs are delivered to the adder 21. As a result, the output of the adder 21, which is the output of the pulse shaper 5, produces a signal whose width is proportional to the amplitude of oscillations of the body center of gravity in respective planes (FIG. 4c). That signal is applied to the control input of the multivibrator 7. Further operation of the electronic ergometer 1 of this embodiment is similar to that described for the electronic ergometer 1 with a single seismic pickup.

The operation of the electronic ergometer 1 during the monitoring and indication of the permissible magnitude of the work performed by the individual 3 is as follows. Prior to operation, the switches 23, 24 of the permissible magnitude selector unit 22 are operated to connect the output 26 of the third bit position and the output 27 of the fourth bit position of the four-digit counter 12 to the inputs of the comparison circuit 25.

With the switches 23 and 24 in respective positions, certain codewords appear at the outputs of the third and fourth bit positions of the four-digit counter 12. When the codewords at the outputs 26, 27 of the four-digit counter 12 coincide with the codewords passed via the switches 23. 24 to the inputs of the comparison circuit 25, the output of the latter produces a singal $U_{25}$ "Reserve used up" (FIG. 4f). The signal from the output of the comparison circuit 25 is a signal "Reserve used up" available from the output of the permissible magnitude selector unit 22 and applied to the enable input of the frequency divider 10 to turn off the latter (FIG. 4e). That signal $U_{25}$ is applied to the enable input of the multivibrator 7 to cause its continuous operation generating $U_7$ (FIG. 4d and 4g). At the same time, that signal is applied to the input of the low frequency multivibrator 28 which thus produces a low frequency signal $U_{28}$ (FIG. 4h). The signals $U_7$ and $U_{28}$ from the outputs of the adjustable high frequency multivibrator 7 and the low frequency multivibrator 28, respectively, are passed to the inputs of the mixer 29 (FIGS. 4g, h). The output of the mixer 29 produces trains of pulses $U_{29}$ (FIG. 4i). The repetition rate of the trains is equal to the frequency of the low frequency multivibrator 28 and the repetition rate of the pulses in each train is equal to the frequency of the high frequency multivibrator 7. The signal from the output of the mixer 29 is applied to the indicator 13.

When activated, the indicator 13 produces an intermittent sound signal and its digital signal lights blink. These alarm signals inform the individual 3 that the reserve of his working capacity is used up. After the signal "Reserve used up" is received, the individual 3 must cease moving and must have a rest. With the "Zero setting" push-button depressed (not shown), the zero setting unit 14 produces a signal $U_{14}$ (FIG. 4j) which causes the cessation of the sound and light alarm signals. This signal $U_{14}$ causes the four-digit counter 12 and the frequency divider 10 to assume the 0 state, with the result that the electronic ergometer 1 also assumes the 0 state.

Cardiac patients, for example, cases with previous myocardial infarction, can utilize the electronic ergometer of the instant invention to extend the range of their movements and a predetermined permissible magnitude of the performed work (the reserve of the working capacity) is used in this case as a control measure. The electronic ergometer of the invention makes it possible to extend the range of movements for cardiac patients during their rehabilitation so that the risk of the recurrence of myocardial infarction is decreased.

The electronic ergometer can help determine labor requirements for some production processes and measure the performed work under domestic conditions during walking or running. Also, the ergometer allows for the estimation of the work performed by athletes during training or match. In all the above cases, the ergometer can be used without previously setting the permissible magnitude of the work being performed.

The ergometer is a portable apparatus and can be carried by the person under test.

While a preferred arrangement has been shown in illustrating the invention, it is to be noted that various changes in detail and arrangement may be made without departing from the spirit and scope of this disclosure.

What is claimed is:

1. An electronic ergometer for measuring work performed by an individual in terms of oscillation of the body center of gravity thereof, comprising:
   a power supply unit having an output;
   transducer means for converting the oscillations of the body center of gravity of said individual into electrical signals provided as an output, said transducer means being implemented as at least one siesmic pickup having an output;
   a pulse shaper comprising a threshold element and having a first input, a second input and an output, said first input being coupled to said output of said power supply unit, and said second input being coupled to said output of said transducer means;
   an adjustable high frequency multivibrator having a control input, an input and an output of settable frequency, said cntrol input being coupled to said output of said pulse shaper, and said input being coupled to said output of said power supply unit;
   a frequency generating circuit operatively associated with said adjustable high frequency multivibrator, having an element for setting the frequency of said output of said adjustable high frequency multivibrator;
   selecting means having an output coupled to said element of said frequency generating circuit for selecting the frequency of said adjustable high frequency multivibrator;
   a frequency divider having a counting input, a reset input, an input and an output, said counting input being coupled to said output of said adjustable high frequency multivibrator, and said input being coupled to said output of said power supply unit;
   a multi-digit counter having a counting input, a reset input, an input and a plurality of bit position outputs equal in number to the number of bit positions of the counter, said counting input being coupled to said output of said frequency divider, and said input being coupled to said output of said power supply unit;
   an indicator having a group of inputs, respective inputs of said group of inputs being coupled to corresponding respective bit position outputs of said multi-digit counter;
   a zero setting unit having an input and an output, said input being coupled to said output of said power supply unit, said output being coupled to said reset input of said frequency divider and to said reset input of said multi-digit counter; and
   a housing to accommodate said transducer means, said pulse shaper, said adjustable high frequency multivibrator, said selecting means, said frequency divider, said multi-digit counter, said indicator, and said zero setting unit.

2. An electronic ergometer as claimed in claim 1, wherein said transducer means include a plurality of seismic pickups provided with respective outputs;
   said pulse shaper including a plurality of threshold elements equal in number to the number of said seismic pickups of said transducer means;
   each of said plurality of threshold elements having an input and an output, said input of each said threshold element being coupled to the output of a respective seismic pickup of said plurality of seismic pickups;
   said pulse shaper further comprising an adder having a plurality of inputs equal in number to the number of said threshold elements and said adder having an output, said inputs being coupled to said outputs of said threshold elements, and said output of said adder being coupled to said control input of said adjustable high frequency multivibrator.

3. An electronic ergometer as claimed in claim 1, wherein said adjustable high frequency multivibrator includes an enable input;
   said frequency divider including an enable input;
   said ergometer further comprising additional selecting means for selecting the permissible magnitude of the work performed by said individual, said additional selecting means having a first input, a second input, a third input, and an output, said first and second inputs being coupled, respectively, to the two highest order bit position outputs of said multi-digit counter, said third input being coupled to said output of said power supply unit, and said output being coupled to said enable input of said adjustable high frequency multivibrator and to said enable input of said frequency divider;
   said additional selecting means further comprising a first switch coupled to said output of said multi-digit counter and providing a first output comprising the output of the highest order bit position of said counter, a second switch coupled to said output of said multi-digit counter and providing a second output comprising the output of the next highest order bit position of said counter, and a comparison circuit having a first input, a second input and an output, said first input of said comparison circuit being coupled to said first output of said first switch, said second input of said comparison circuit being coupled to said second output of said second switch, and said output of said comparison circuit being coupled to said enable input of said adjustable high frequency multivibrator and to said enable input of said frequency divider;
   said ergometer further comprising a low frequency multivibrator having a first input, a second input and an output, said first input beng coupled to said output of said comparison circuit, and said second input being coupled to said output of said power supply unit;
   said indicator having an additional input, said ergometer further comprising a mixer having a first input, a second input, a third input and an output, said first input being coupled to said output of said adjustable high frequency multivibrator, said second input being coupled to said output of said low frequency multivibrator, said third input being coupled to said output of said power supply unit, and said output being coupled to said additional input of said indicator.

4. An electronic ergometer as claimed in claim 2, wherein said adjustable high frequency multivibrator includes an enable input;

said frequency divider having an enable input;

said ergometer further comprising additional selectig means for selecting the permissible magnitude of the work performed by said individual, said additional selecting means having a first input, a second input, a third input, and an output, said first and second inputs being coupled, respectively, to the two highest order bit position ouputs of said multi-digit counter, said third input being coupled to said output of said power supply unit, and said output being coupled to said enable input of said adjustable high frequency multivibrator and to said enable input of said frequency divider;

said additional selecting means further comprising a first switch coupled to said output of said multi-digit counter and providing a first output comprising the output of the highest order bit position of said counter, a second switch coupled to said output of said multi-digit counter and providing a second output comprising the output of the next highest order bit position of said counter, and a comparison circuit having a first input, a second input and an output, said first input of said comparison circuit being coupled to said first output of said first switch, said second input of said comparison circuit being coupled to said second output of said second switch and said output of said comparison circuit being coupled to said enable input of said adjustable high frequency multivibrator and to said enable input of said frequency divider;

said ergometer further comprising a low frequency multivibrator having a first input, a second input and an output, said first input being coupled to said output of said comparison circuit, and said second input being coupled to said output of said power supply unit;

said indicator having an additional input, said ergometer further comprising a mixer having a first input, a second input, a third input an an output, said first input being coupled to said output of said adjustable high frequency multivibrator, said second input being coupled to said output of said low frequency multivibrator, said third input being coupled to said output of said power supply unit, and said output being coupled to said additional input of said indicator.

* * * * *